Jan. 1, 1974 H. S. MASON Plant Pat. 3,418
APPLE TREE
Filed Oct. 15, 1971
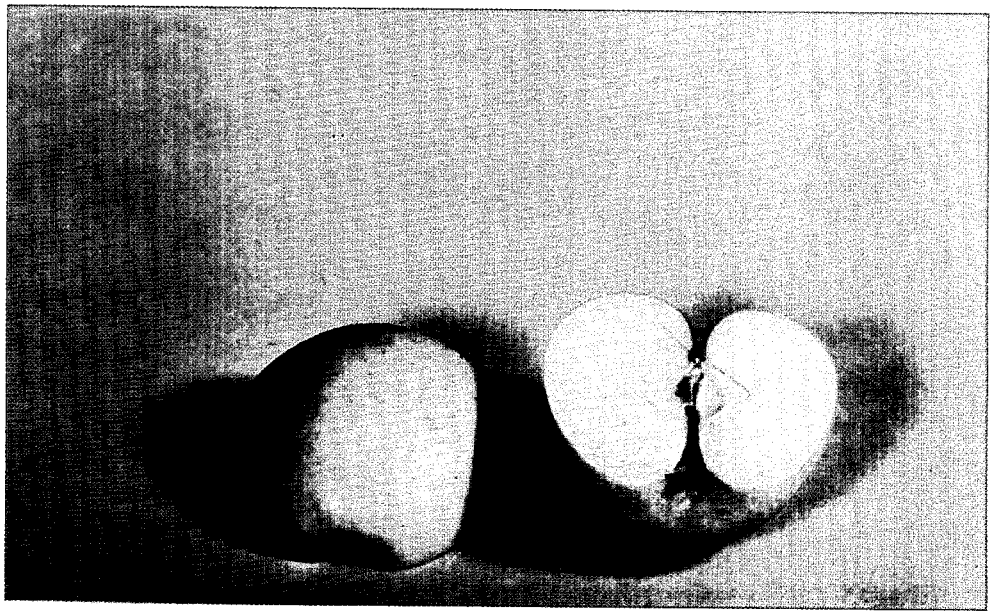
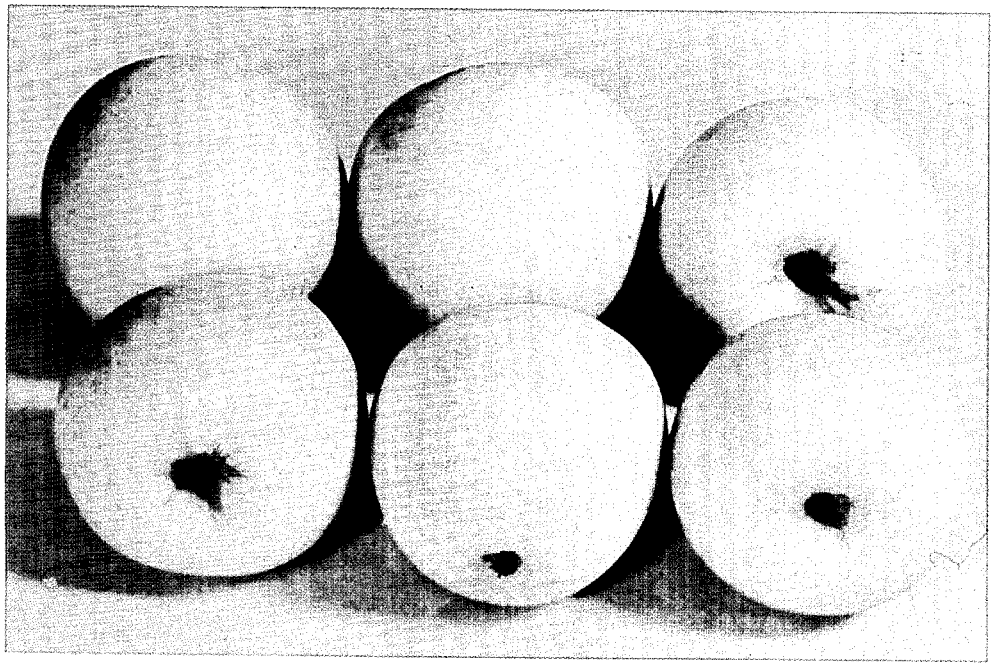

United States Patent Office

Plant Pat. 3,418
Patented Jan. 1, 1974

3,418

APPLE TREE

Herbert S. Mason, 1210 Gilmer Ave.,
Tallassee, Ala. 36078

Filed Oct. 15, 1971, Ser. No. 189,681
Int. Cl. A01h *5/03*
U.S. Cl. Plt.—34 1 Claim

ABSTRACT OF THE DISCLOSURE

An apple tree which was discvered as a bud mutation of the variety Golden Delicious Gilbert strain (Plant Pat. No. 202). In contrast with its parent, the fruit of the new variety has a brilliant yellow color, with non-russeting characteristics, which fruit matures approximately one and one-half weeks before Golden Delicious, Gilbert strain (Plant Pat. No. 202).

The present new variety of apple tree is a bud sport (bud mutation) of the variety Golden Delicious, Gilbert strain (Plant Pat. No. 202), and was found in the orchard of Herbert S. Mason, Tallassee, Ala. in the spring of 1963. Trees of the sport were budded and planted in the Mason orchard, Tallassee, Ala. The plants are vigorous and produce fruit of execllent shape and color. The fruit matures at approximately one and one-half weeks earlier than Golden Delicious—the first to second week in August, in Tallassee, Ala.

The accompanying drawing comprises color photographs of the fruit of the new variety shown in axial section, singly and in multiple.

In the following description, color illustrations conform to those used in the Nickerson Color Fan, maximum chroma, 40 hues, published by the Nickerson Color Company, Inc.

The color illustration of one of the apples shows a pink blush which appears when the fruit is exposed to strong sunlight in the ripening process.

Tree.—Tree is semidwarf, with vigorous growth. Form of the tree is roundish or spreading, somewhat drooping with sub-acute angles of branching. Bark of the trunk and older branches mostly light gray splotched over light reddish brown. Lenticels prominent on young branches; bark has weakly grayish glaucous covering on light reddish brown. Twigs stout with numerous thick spurs; stipules prominent.

Vegetative buds are numerous, small and pubescent.

Leaf glabrous, margin medium dentate serration. Leaf tip acute acuminate, occasionally elliptical, equilateral base, midrib priminent glabrous or slightly pubescent. Leaf scars are prominent, lens shaped. Upper leaf surface is grayish green 1 GY 3/2. Lower leaf surface is moderate olive green 2.5 GY 4/3. Mature leaf has a length 3½ to 4 inches, leaf width 1¾ to 2 inches.

Flower.—Flower buds are large with red scales and pink flowers.

Fruit exterior.—Form oblong brilliant yellow, 65 Y 9/9, non-russeting at Tallassee, Ala. The fruit averages approximately 3¼ inches in axial dimension and approximately 3¼ inches in transverse dimension. Lenticels are numerous, small, dark center with yellow halo. Calyx tube is funnel-shaped, stamens basal. Basin is shallow, conic, symmetrical.

Fruit interior.—Core is open, medium size, abaxial, cells open, core lines clasping, typically 5 locules with 2 seeds per locule. Endocarp is typical, brilliant greenish yellow 7.5 and 9/8. Accessory tissue is brilliant greenish yellow 7.5 Y 9/8, firm, moderately fine, somewhat crisp, tender, moderately juicy, sweet, excellent, delicious flavor.

As grown in Alabama, this variety is an excellent commercial and home garden variety. The fruit is very beautiful, free from russeting, of a brilliant yellow, highly flavored for a dessert and cooking apple. The fruit is the same size as Golden Delicious. In Alabama it has produced well at Tallassee in central Alabama. The fruit is mature with adequate sugar when first color has developed. The fruit matures approximately one and one-half weeks before Golden Delicious. The absence of russeting on this sport of Golden Delicious makes it highly valuable to the commercial grower.

Under favorable conditions, the tree is an excellent producer. It bears fruit early on semidwarf rootstock. It is recommended for general commercial and home garden planting as an excellent type for market before Vance Red Delicious fruit is ready for harvest.

I claim:

1. A new and distinct variety of apple tree characterized particularly by the earlier maturing of the fruit, brilliant yellow color, non-russeting, as contrasted with its parent variety, Golden Delicious, substantially as shown and described.

No references cited.

ROBERT E. BAGWILL, Primary Examiner